(12) United States Patent
Morinaga et al.

(10) Patent No.: US 12,274,788 B2
(45) Date of Patent: Apr. 15, 2025

(54) PARTICULATE POLY(LACTIC-CO-GLYCOLIC) ACID, METHOD FOR MANUFACTURING PARTICULATE POLY (LACTIC-CO-GLYCOLIC) ACID, AND PARTICULATE POLY(LACTIC-CO-GLYCOLIC) ACID MANUFACTURING APPARATUS

(71) Applicant: RICOH COMPANY, LTD., Tokyo (JP)

(72) Inventors: Tadahiko Morinaga, Kanagawa (JP); Tatsuru Moritani, Kanagawa (JP); Tatsuki Yamaguchi, Kanagawa (JP); Masaru Ohgaki, Kanagawa (JP); Shinji Aoki, Kanagawa (JP); Yuichi Sato, Kanagawa (JP)

(73) Assignee: Ricoh Company, Ltd., Tokyo (JP)

(*) Notice: Subject to any disclaimer, the term of this patent is extended or adjusted under 35 U.S.C. 154(b) by 25 days.

(21) Appl. No.: 17/525,521

(22) Filed: Nov. 12, 2021

(65) Prior Publication Data
US 2022/0062178 A1 Mar. 3, 2022

Related U.S. Application Data

(62) Division of application No. 15/704,106, filed on Sep. 14, 2017, now abandoned.

(30) Foreign Application Priority Data

Sep. 27, 2016 (JP) .................................. 2016-188507
Aug. 22, 2017 (JP) .................................. 2017-159011

(51) Int. Cl.
*A61K 9/16* (2006.01)
*B01J 2/04* (2006.01)
*B01J 2/18* (2006.01)
*C08G 63/06* (2006.01)
*A61K 9/51* (2006.01)
*B29B 9/10* (2006.01)
*B29B 9/12* (2006.01)

(52) U.S. Cl.
CPC .............. *A61K 9/1647* (2013.01); *B01J 2/04* (2013.01); *B01J 2/18* (2013.01); *C08G 63/06* (2013.01); *A61K 9/5153* (2013.01); *A61K 9/5192* (2013.01); *B29B 9/10* (2013.01); *B29B 9/12* (2013.01); *B29B 2009/125* (2013.01)

(58) Field of Classification Search
CPC .......... A61K 9/1647; B01J 2/18; C08G 63/06
See application file for complete search history.

(56) References Cited

U.S. PATENT DOCUMENTS 6,367,925 B1* 4/2002 Hayes ........................ B41J 3/36
347/109
6,998,074 B1* 2/2006 Radulescu ........... A61K 9/1682
264/4.1
11,654,116 B2* 5/2023 Shiraishi ............... A61K 9/1694
424/489
2006/0204481 A1* 9/2006 Steer ........................ A61K 31/56
514/169
2008/0145439 A1 6/2008 Lobl et al.
2010/0104970 A1 4/2010 Norikane et al.
2010/0330147 A1 12/2010 Hossainy et al.
2013/0010035 A1 1/2013 Norikane et al.
2014/0272695 A1 9/2014 Moritani et al.
2015/0261111 A1* 9/2015 Inoue ................... G03G 9/0804
430/108.4

FOREIGN PATENT DOCUMENTS

| CN | 104013955 | 9/2014 |
|---|---|---|
| JP | 2006131577 | 5/2006 |
| JP | 2007003780 | 1/2007 |
| JP | 2007199463 | 8/2007 |
| JP | 2008292976 | 12/2008 |
| JP | 2010031003 | 2/2010 |
| JP | 2010102195 | 5/2010 |
| JP | 2010150151 | 7/2010 |
| JP | 2011111429 | 6/2011 |
| JP | 2011194675 | 10/2011 |
| JP | 2014178397 | 9/2014 |

(Continued)

OTHER PUBLICATIONS

McCall RL, Sirianni RW. PLGA nanoparticles formed by single- or double-emulsion with vitamin E-TPGS. J Vis Exp. Dec. 27, 2013;(82):51015. (Year: 2013).*

Sah, Edel, and Hongkee Sah. "Recent trends in preparation of poly (lactide-co-glycolide) nanoparticles by mixing polymeric organic solution with antisolvent." Journal of Nanomaterials 16.1 (2015): 61-61. (Year: 2015).*

Reis, Catarina Pinto, et al. "Design of polymeric nanoparticles and its applications as drug delivery systems for acne treatment." Drug development and industrial pharmacy 40.3 (2014): 409-417. (Year: 2014).*

(Continued)

*Primary Examiner* — Abigail Vanhorn (74) *Attorney, Agent, or Firm* — Grüneberg and Myers PLLC (57) ABSTRACT

A particulate poly(lactic-co-glycolic) acid (PLGA) is provided. The particulate PLGA comprises a poly(lactic-co-glycolic) acid (PLGA), and has an average volume-based panicle diameter of 80 nm or less and a relative span factor (R.S.F.) satisfying the following formula (1):

$$0 < R.S.F. \leq 1.20 \quad \text{Formula (1)}$$

where R.S.F. is defined by (D90−D10/D30, where D90, D50, and D10 respectively represent particle diameters at cumulative rates of 90%, 50%, and 10% by volume based on a cumulative particle size distribution counted from a small-particle side.

12 Claims, 4 Drawing Sheets

(56) References Cited

FOREIGN PATENT DOCUMENTS

| WO | 2012/042274 | A1 | † | 4/2012 |
| WO | 2017/103113 | A2 | † | 6/2017 |

OTHER PUBLICATIONS

Murakami, Hideki, et al. "Preparation of poly (DL-lactide-co-glycolide) nanoparticles by modified spontaneous emulsification solvent diffusion method." International journal of pharmaceutics 187.2 (1999): 143-152. (Year: 1999).*

Budhian et al., "*Haloperidol-loaded PLGA nanoparticles: Systematic study of particle size and drug content*", International Journal of Pharmaceutics, vol. 336, 2007, pp. 367-375.

Dangi et al., "*Preparation, optimization and characterization of PLGA nanoparticle*", International Journal of Pharmacy & Life Sciences, vol. 4, No. 7, 2013, pp. 2810-2818.

De Oliveira et al., "*Physicochemical aspects behind the size of biodegradable polymeric nanoparticles: A step forward*", Colloids and Surfaces A: Physicochemical and Engineering Aspects vol. 436, 2013, pp. 1092-1102.

Fornaguera et al., "*Electrolytes as a tuning parameter to control nano-emulsion andnanoparticle size*", RSC Advances, 2016, pp. 58203-58211.

Choi et al., "*Size-controlled biodegradable nanoparticles: Preparation and size-dependent cellular uptake and tumor cell growth inhibition*", Colloids and Surfaces B: Biointerfaces, vol. 122, 2014, pp. 545-551.

Freag et al., "*Stealth, biocompatible monoolein-based lyotropic liquid crystalline nanoparticles for enhanced aloe-emodin delivery to breast cancer cells: in vitro and vivo studies*", International Journal of Nanomedicine, vol. 11, 2016, pp. 4799-4818.

Karnik et al., "*Microfluidic Platform for Controlled Synthesis of Polymeric Nanoparticles*", Nano Letters, vol. 8, No. 9, 2008, pp. 2906-2912.

Mondal et al.,"*Effect of Different Formulation Variables on Some Particle Characteristics of Poly (DL-lactide-co-glyclolide) Nanoparticles*", Yakugaku Zasshi, vol. 128, No. 4, 2008, pp. 595-601.

Pedraz et al., "*Solid Lipid and polymeric Nanoparticles for Drug Delivery*", Nanotechnologies for the Life Sciences, vol. 10, 2007, pp. 471-508.

Vandervoort et al., "*Biocompatible stabilizers in the preparation of PLGA nanoparticles: a factorial design study*", International Journal of Pharmaceutics, vol. 238, 2002, pp. 77-92.

Vega et al., "*PLGA Nanospheres for the Ocular Delivery of Flurbiprofen: Drug Release and Interactions*", Journal of Pharmaceutical Sciences vol. 97, No. 12, 2008, pp. 5306-5317.

Konica Minolta Industrial Inkjet KM512 Series Webpage, retrieved Dec. 28, 2022 from.†

\* cited by examiner
† cited by third party

PARTICULATE POLY(LACTIC-CO-GLYCOLIC) ACID, METHOD FOR MANUFACTURING PARTICULATE POLY (LACTIC-CO-GLYCOLIC) ACID, AND PARTICULATE POLY(LACTIC-CO-GLYCOLIC) ACID MANUFACTURING APPARATUS

CROSS-REFERENCE TO RELATED APPLICATIONS

This patent application is a divisional of U.S. application Ser. No. 15/704,106, filed on Sep. 14, 2017, which is based on and claims priority pursuant to 35 U.S.C. § 119(a) to Japanese Patent Application Nos. 2016-188507 and 2017-159011, filed on Sep. 27, 2016 and Aug. 22, 2017, respectively, in the Japan Patent Office, the entire disclosure of each of which is hereby incorporated by reference herein.

BACKGROUND

Technical Field

The present disclosure relates to a particulate poly(lactic-co-glycolic) acid (PLGA), a method for manufacturing particulate PLGA, and a particulate PLGA manufacturing apparatus.

Description of the Related Art

Drug delivery systems are actively researched these days as technologies for effectively and safely delivering medical ingredients to disease sites. One example of drug delivery systems involves drug-encapsulated nano particles. Such nano particles are capable of passing through micropores, such as capillary vessels, as the particle size is adjusted to several tens to several hundreds nanometers. For this reason, drug-encapsulated nano particles are increasingly in demand.

The drug-encapsulated nano particles are preferably composed of highly-biocompatible materials which are capable of sustained-releasing the encapsulated drug. Examples of such materials include polylactic acid (PLA) and poly(lactic-co-glycolic) acid (PLGA). In particular, PLGA has been researched more actively since PLGA is capable of storing the encapsulated drug for an extended period of time.

For medical application, it is necessary that the nano particles be subjected to sterilization treatments such as heating, radiation irradiation, and filtration. However, for PLGA particles, heating sterilization treatments are unsuitable because PLGA particles can melt due to their low glass transition temperatures of about 30° C. to 50° C. Radiation irradiation is also unsuitable because there is a possibility of denaturing nano particles. Thus, for PLGA particles to be used for medical applications, filtration sterilization is suitable.

There is a need for PLGA particles suitable for filtration sterilization.

SUMMARY

In accordance with some embodiments of the present invention, a particulate poly(lactic-co-glycolic) acid (PLGA) is provided. The particulate PLGA comprises a poly(lactic-co-glycolic) acid (PLGA), and has an average volume-based particle diameter of 80 nm or less and a relative span factor (R.S.F.) satisfying the following formula (1):

$$0 < R.S.F. \leq 1.20 \qquad \text{Formula (1)}$$

where R.S.F. is defined by $(D90-D10)/D50$, where D90, D50, and D10 respectively represent particle diameters at cumulative rates of 90%, 50%, and 10% by volume based on a cumulative particle size distribution counted from a small-particle side.

In accordance with some embodiments of the present invention, a method for manufacturing particulate poly(lactic-co-glycolic) acid (PLGA) is provided. The method includes dissolving a poly(lactic-co-glycolic) acid (PLGA) in a good solvent of the PLGA to obtain a PLGA solution; and discharging the PLGA solution from at least one discharge hole having an inner diameter of less than 1.0 mm into a poor solvent of the PLGA.

In accordance with some embodiments of the present invention, a particulate poly(lactic-co-glycolic) acid (PLGA) manufacturing apparatus is provided. The PLGA manufacturing apparatus includes a PLGA solution storage, a solution discharger, and a poor solvent storage. The PLGA solution storage stores a PLGA solution in which a poly(lactic-co-glycolic) acid (PLGA) is dissolved in a good solvent of the PLGA. The solution discharger has at least one discharge hole having an inner diameter of less than 1.0 mm, and is connected to the PLGA solution storage. The poor solvent storage stores a poor solvent of the PLGA.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

The accompanying drawings are intended to depict example embodiments of the present invention and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Embodiments of the present invention are described in detail below with reference to accompanying drawings. In describing embodiments illustrated in the drawings, specific terminology is employed for the sake of clarity. However, the disclosure of this patent specification is not intended to be limited to the specific terminology so selected, and it is to be understood that each specific element includes all technical equivalents that have a similar function, operate in a similar manner, and achieve a similar result.

For the sake of simplicity, the same reference number will be given to identical constituent elements such as parts and materials having the same functions and redundant descriptions thereof omitted unless otherwise stated.

In accordance with some embodiments of the present invention, a particulate PLGA suitable for filtration sterilization is provided.

Particulate PLGA

The particulate PLGA in accordance with some embodiments of the present invention contains at least a poly(lactic-co-glycolic) acid (PLGA). The particulate PLGA preferably contains a physiologically active substance, and optionally contains other components, such as a dispersant and an additive, as necessary.

The particulate PLGA may have such a configuration that the physiologically active substance and other optional components are dispersed in the matrix of the poly(lactic-co-glycolic) acid (PLGA).

As a result of intensive studies of the inventors of the present invention, a particulate PLGA is provided that is suitable for filtration sterilization.

Filtration sterilization is generally performed to remove bacteria, such as microbes, from sterilization objects by using a membrane filter having a pore diameter of 0.2 μm. Therefore, nano PLGA particles having a particle diameter in excess of 200 nm cannot sufficiently pass through the filtration sterilization filter.

In view of this, PLGA particles having an average particle diameter of 200 nm or less have been proposed.

On the other hand, bacteria having shape plasticity, such as *mycoplasma*, and much smaller bacteria should be removed with a membrane filter having a pore diameter of 0.1 μm. In this case, the inventors of the present invention have found that not only the particle size of nano PLGA particles should be 100 nm or less but also the particle size distribution thereof should be taken into consideration. In particular, the inventors have found that the sterilization rate lowers as the particle size distribution becomes larger. This is because coarse particles that cannot pass the filter increase in number.

As a result, the inventors have found an appropriate particle size distribution for filtration sterilization.

Properties of Particulate PLGA

Average Volume-Based Particle Diameter

The particulate PLGA has an average volume-based particle diameter of 80 nm or less, preferably from 10 to 50 nm, more preferably from 10 to 40 nm, and most preferably from 10 to 30 nm.

The average volume-based particle diameter of the particulate PLGA can be measured with a Fiber-Optics Particle Analyzer (FPAR-1000 available form Otsuka Electronics Co., Ltd.) employing a dynamic light scattering method for measuring thick systems.

In accordance with some embodiments of the present invention, the particulate PLGA has an average volume-based particle diameter of 80 nm or less. When the average volume-based particle diameter is in excess of 80 nm, the filtration sterilization filter will be easily clogged with the particles. In a case in which the sterilization target is cancer, the average volume-based particle diameter is preferably in the range of from 10 to 30 nm.

Relative Span Factor (R.S.F.)

The particulate PLGA according to an embodiment of the present invention has a relative span factor (R.S.F.) satisfying the following formula (1).

$$0 < R.S.F. \leq 1.20 \qquad \text{Formula (1)}$$

R.S.F. is defined by (D90-D10)/D50.

D90, D50, and D10 respectively represent particle diameters at cumulative rates of 90%, 50%, and 10% by volume based on a cumulative particle size distribution counted from a small-particle side.

When R.S.F. is greater than 1.20, it means that the number of coarse particles that cannot pass the filter is so large that the sterilization rate degrades.

R.S.F. can be measured with a Fiber-Optics Particle Analyzer (FPAR-1000 available form Otsuka Electronics Co., Ltd.) employing a dynamic light scattering method for measuring thick systems.

Poly(lactic-co-glycolic) Acid (PLGA)

Poly(lactic-co-glycolic) acid (PLGA) is a copolymer having a structural unit derived from lactic acid and another structural unit derived from glycolic acid.

In the present disclosure, poly(lactic-co-glycolic) acid may be simply referred to as PLGA.

Preferably, the poly(lactic-co-glycolic) acid (PLGA) has a weight average molecular weight of from 2,000 to 250,000, more preferably from 2,000 to 100,000, much more preferably from 3,000 to 50,000, and most preferably from 5,000 to 10,000.

Preferably, in the poly(lactic-co-glycolic) acid (PLGA), the molar ratio (L:G) between a structural unit (L) derived from lactic acid and another structural unit (G) derived from glycolic acid is from 1:99 to 99.1 more preferably from 25:75 to 99:1, much more preferably from 30:70 to 90:10, and most preferably from 50:50 to 85:15.

The poly(lactic-co-glycolic) acid (PLGA) may be prepared by heating lactic acid and glycolic acid in the presence of an ion-exchange resin, serving as a catalyst, under weakly-reduced pressure to cause a condensation polymerization.

In preparing the poly(lactic-co-glycolic) acid (PLGA), the lactic acid may be replaced with lactide.

The poly(lactic-co-glycolic) acid (PLGA) is also commercially available. For example, the PLGA is available from Wako Pure Chemical industries, Ltd. or Taki Chemical Co., Ltd.

The content rate of poly(lactic-co-glycolic) acid (PLGA) in the particulate PLGA is preferably 1% by mass or more, more preferably from 1% to 100% by mass, much more preferably from 10% to 99% by mass, yet more preferably from 30% to 95% by mass, and most preferably from 50% to 90% by mass.

Physiologically Active Substance

Specific examples of the physiologically active substance include, but are not limited to, medical compounds, functional food compounds, and functional cosmetic compounds.

The particulate PLGA containing a medical compound is preferably used for medicines.

The particulate PLGA containing a functional food compound is preferably used for foods.

The particulate PLGA containing a cosmetic compound is preferably used for cosmetics.

Medicine

The medicine contains a medical compound and optionally other components, such as a dispersant and an additive, as necessary.

The medicine may be in a solid dosage form such as tablet, capsule, and suppository; an aerosol for pulmonary or intranasal administration; or a liquid dosage form for injection or intraocular, intra-aural, or oral administration.

By containing a dispersant and/or an additive, the particulate PLGA may be manufactured as a functional particulate or a medical composition.

Specific examples of the functional particulate include, but are not limited to, prompt-release particulate, sustained-release particulate. pH-dependent-release particulate, pH-independent-release particulate, enteric coating particulate, controlled-release coating particulate, and nanocrystal-containing particulate. Each of these functional particulates can be used alone or in combination with others.

Specific examples of the medical composition include, but are not limited to, colon-targeted drug delivery formulations, lipid microsphere formulations, dry emulsion formulations, self-emulsification formulations, dry syrups, powder formulations for nasal or pulmonary administration, wax matrix formulations, hydrogel formulations, polymer micelle formulations, mucoadhesion formulations, gastric floating formulations, liposome formulations, and solid dispersion formulations. Each of these medical compositions can be used alone or in combination with others.

The medicine may be either a medical composition or an active pharmaceutical ingredient.

Medical Compound

The medical compound has no limitation so long as it is capable of becoming the functional particulate or medical composition. Examples of the medical compound include poorly-water-soluble compounds, but are not limited thereto.

The poorly-water-soluble compounds refer to compounds, the logarithmic value of water/octanol partition coefficient of which is of 3 or more. The water/octanol partition coefficient can be measured according to the Shake flask method described in the specification of JIS (Japanese Industrial Standards) Z 7260-107 (2000).

Examples of the medical compound involve all compounds effective as a medicine in all possible forms (e.g., salt, hydrate).

Specific examples of the poorly-water-soluble compounds include, but are not limited to, griseofulvin, itraconazole, norfloxacin, tamoxifen, cyclosporine, glibenclamide, troglitazone, nifedipine, phenacetin, phenytoin, digitoxin, nilvadipine, diazepam, chloramphenicol, indometacin, nimodipine, dihydroergotoxine, cortisone, dexamethasone, naproxen, tulobuterol, beclometasone dipropionate, fluticasone propionate, pranlukast, tranilast, loratadine, tacrolimus, amprenavir, bexarotene, calcitriol, clofazimine, digoxin, doxercalciferol, dronabinol, etoposide, isotretinoin, lopinavir, ritonavir, progesterone, saquinavir, sirolimus, tretinoin, valproic acid, amphotericin, fenoldopam, melphalan, paricalcitol, propofol, voriconazole, ziprasidone, docetaxel, haloperidol, lorazepam, teniposide, testosterone, and valrubicin. Among these compounds, cyclosporine is preferable.

Functional Food Compound

Specific examples of the functional food compound include, but are not limited to, vitamin A, vitamin D, vitamin E, lutein, zeaxanthin, lipoic acid, flavonoid, and fatty acids (e.g., omega-3 fatty acid, omega-6 fatty acid). Each of these compounds can be used alone or in combination with others.

Food

The food contains a functional food compound and optionally other components, such as a dispersant and an additive, as necessary.

Specific examples of the food include, but are not limited to frozen desserts such as ice cream, sherbet, and shaved ice; noodles such as buckwheat noodle, wheat noodle, vermicelli, coating doughs for dumplings (e.g., jiaozi and shaomai), Chinese noodle, and instant noodle; confectioneries such as candy, gum, chocolate, tablet candy, snack, biscuit, jelly, jam, cream, baked confectionery, and bread; seafoods such as crab, salmon, clam, tuna, sardine, shrimp, skipjack tuna, mackerel, whale, oyster, saury, squid, bloody clam, scallop, abalone, sea urchin, salmon roe, and Japanese abalone; processed marine and livestock products such as kamaboko (boiled fish paste), ham, and sausage; dairy products such as processed milk and fermented milk; oils and fats and processed foods thereof, such as salad oil, tempura oil, margarine, mayonnaise, shortening, whip cream, and dressing; seasonings such as sauce and baste; retort pouch foods of curry, stew, oyakodon (bowl of rice topped with chicken and eggs), congee, rice porridge, chūkadon (bowl of rice topped with starch sauce of vegetable, meat, etc.), katsudon (bowl of rice topped with pork cutlet), tendon (bowl of rice topped with tempura), unadon (bowl of rice topped with eel), rice with hashed meat, oden (vegetables, fish dumplings and various other articles of food stewed in a thin soy soup), mapo doufu, gyūdon (bowl of rice topped with beef), spaghetti with meat sauce, egg soup, omurice (omelet with a filling of ketchup-seasoned fried rice), jiaozi, shaomai, hamburg steak, and meat ball; and health foods and nutritional supplementary foods in various forms.

Functional Cosmetic Compound

Specific examples of the functional cosmetic compound include, but are not limited to, alcohols, fatty alcohols, polyols, aldehydes, alkanolamines, alkoxylated alcohols (e.g., polyethylene glycol derivatives of alcohols and fatty alcohols), alkoxylated amides, alkoxylated amines, alkoxylated carboxylic acids, amides including salts (e.g., ceramides), amines, amino acids including salts and alkyl-substituted derivatives, esters, alkyl-substituted and acyl derivatives, polyacrylic acids, acrylamide copolymers, adipic acids copolymers, aminosilicones, biological polymers and derivatives thereof, butylene copolymers, carbohydrates (e.g., polysaccharides, chitosan, and derivatives thereof), carboxylic acids, carbomers, esters, ethers, polymer ethers (e.g., PEG derivatives, PPG derivatives), glyceryl esters and derivatives thereof, halogen compounds, heterocyclic compounds including salts, hydrophilic colloids and derivatives including salts and rubbers (e.g., cellulose derivatives, gelatin, xanthane gum, natural rubbers), imidazolines, inorganic substances (e.g., clay, $TiO_2$, $ZnO$), ketones (e.g., camphor), isethionates, lanoline and derivatives thereof, organic salts, phenols including salts (e.g., paraben), phosphor compounds (e.g., phosphoric acid derivatives), polyacrylates and acrylate copolymers, proteins and enzyme derivatives (e.g., collagen), synthetic polymers including salts, siloxanes and silanes, sorbitan derivatives, sterols, sulfonic acids and derivatives thereof, and waxes. Each of these compounds can be used alone or in combination with others.

Cosmetics

The cosmetics contain a functional cosmetic compound and optionally other components, such as a dispersant and an additive, as necessary.

Examples of the cosmetics include, but are not limited to, skin-care cosmetics, make-up cosmetics, hair-care cosmetics, body-care cosmetics, and fragrance cosmetics.

Specific examples of the skin-care cosmetics include, but are not limited to, cleansing composition for removing makeup, face wash, milky lotion, skin lotion, beauty essence, skin moisturizer, facial pack, and cosmetics for shaving (e.g., shaving foam, pre-shave lotion, after-shave lotion).

Specific examples of the make-up cosmetics include, but are not limited to, foundation, lipstick, and mascara.

Specific examples of the hair-care cosmetics include, but are not limited to, hair shampoo, hair conditioner, hair treatment, and hair dressings (e.g., hair gel, hair set lotion, hair liquid, hair mist).

Specific examples of the body-care cosmetics include, but are not limited to, body soap, sunscreen, and massage cream.

Specific examples of the fragrance cosmetics include, but are not limited to, perfumes (e.g., perfume, parfum), eau de parfums (e.g., perfume cologne), eau de toilettes (e.g., perfume de toilette, parfum de toilette), and eau de colognes (e.g., cologne, fresh cologne).

The content rate of the physiologically active substance in the particulate PLGA is preferably in the range of from 5% to 95% by mass, and more preferably from 5% to 50% by mass.

Dispersant

The dispersant is preferably used for dispersing the physiologically active substance.

Examples of the dispersant include low-molecular-weight dispersants and high-molecular-weight dispersant polymers.

The low-molecular-weight dispersants refers to compounds having a weight average molecular weight of less than 15.000. The high-molecular-weight dispersant polymers refer to compounds having a weight average molecular weight of 15,000 or above and at least one repeating covalent bond between the monomers.

The low-molecular-weight dispersants have no limit as long as they are acceptable as physiologically active substances for medicine, etc. Specific examples of such dispersants include, but are not limited to, lipids, sugars, cyclodextrins, amino acids, and organic acids. Each of these compounds can be used alone or in combination with others.

Specific examples of the lipids include, but are not limited to, middle-chain or long-chain monoglyceride, diglyceride, and triglyceride, phospholipid, plant oils (e.g., soybean oil, avocado oil, squalene oil, sesame oil, olive oil, corn oil, rapeseed oil, safflower oil, and sunflower oil), fish oil, seasoning oil, water-insoluble vitamin, fatty acid, and mixtures and derivatives thereof. Each of these compounds can be used alone or in combination with others.

Specific examples of the sugars include, but are not limited to, glucose, mannose, idose, galactose, fucose, ribose, xylose, lactose, sucrose, maltose, trehalose, turanose, raffinose, maltotriose, acarbose, water-soluble cellulose, synthetic cellulose, and sugar alcohols such as glycerin, sorbitol, lactitol, maltitol, mannitol, xylitol, erythritol, polyol, and derivatives thereof. Each of these compounds can be used alone or in combination with others.

Other Components

The other components are preferably those for medical use.

Specific examples of such components include, but are not limited to, excipients, corrigents, disintegrants, fluidizers, absorbents, lubricants, odor improving agents, flavoring agents, coloring agents, antioxidants, masking agents, antistatic agents, and wetting agents. Each of these compounds can be used alone or in combination with others.

Method for Manufacturing Particulate PLGA

The method for manufacturing particulate PLGA in accordance with some embodiments of the present invention includes a particle forming process and optionally other processes.

The method for manufacturing particulate PLGA preferably manufactures the above-described particulate PLGA in accordance with some embodiments of the present invention.

The method for manufacturing particulate PLGA falls into emulsion solvent diffusion methods ("ESD methods") that are spheroidizing techniques using an interdiffusion between a good solvent and a poor solvent caused by a surface tension difference thereinbetween.

Specifically, in the ESD method using PLGA, a solution of a PLGA ("PLGA solution") is poured into a poor solvent of the PLGA (i.e., water or an aqueous organic solvent). As the PLGA solution and the poor solvent come into contact with each other, the PLGA solution diffuses and the PLGA comes into contact with the poor solvent. As a result, the PLGA crystallizes to become fine spherical particles.

Particle Forming Process

The particle forming process includes discharging the PLGA solution from at least one discharge hole into a poor solvent of the PLGA. Preferably, the particle forming process further includes a liquid flow treatment and/or a liquid circulation treatment.

PLGA Solution

The PLGA solution is a solution of a PLGA dissolved in a good solvent of the PLGA.

The PLGA solution can be obtained by dissolving a PLGA in a good solvent of the PLGA.

Specific examples of the good solvent include, but are not limited to, alcohols, ketones, ethers, and acetonitrile.

Specific examples of the alcohols include, but are not limited to, alcohols having 1 to 4 carbon atoms. Specific examples of the alcohols having 1 to 4 carbon atoms include, but are not limited to, methanol, ethanol, propanol, and butanol Specific examples of the ketones include, but are not limited to, ketones having 3 to 6 carbon atoms. Specific examples of the ketones having 3 to 6 carbon atoms include, but are not limited to, acetone, methyl ethyl ketone, and cyclohexanone.

Specific examples of the ethers include, but are not limited to, ethers having 2 to 6 carbon atoms. Specific examples of the ethers having 2 to 6 carbon atoms include, but are not limited to, dimethyl ether, methyl ethyl ether, and diethyl ether.

Each of these compounds can be used alone or in combination with others.

In particular, a mixture solvent of an alcohol and a ketone is preferable, and a mixture solvent of ethanol and acetone is more preferable.

In the present disclosure, the good solvent refers to a solvent capable of dissolving the PLGA in large amounts, i.e., the PLGA exhibits a high solubility in the good solvent.

The poor solvent refers to a solvent capable of dissolving the PLGA in small amounts or incapable of dissolving the PLGA, i.e., the PLGA exhibits a low solubility or insolubility in the poor solvent.

Performances of the good solvent and poor solvent can be defined by the mass of the PLGA soluble in 100 g of the solvent at 25° C. In the present disclosure, the good solvent is preferably capable of dissolving the PLGA in an amount of 0.1 g or more. The poor solvent is preferably capable of dissolving the PLGA in an amount of 0.05 g at most.

The content rate of the PLGA in the PLGA solution is preferably 5.0% by mass or less, more preferably from 0.1% to 5.0% by mass, when the solvent is a mixture solvent of acetone and ethanol. When the content rate is 5.0% by mass or less, aggregation of particles and widening of particle size distribution are suppressed.

By controlling the content of the PLGA in the PLGA solution, the particle diameter of the resulting particulate PLGA can be controlled to some extent.

Discharge Hole

The discharge hole has an inner diameter of less than 1.0 mm.

Preferably, the inner diameter is not less than 1.0 μm and less than 1.0 mm.

In a case in which the discharge hole is not in a true circle shape, the discharge hole has an area equivalent to that of a true circle having a diameter of less than 1.0 mm.

The discharge hole may or may not be dipped into the poor solvent. To prevent the PLGA solution from being dried within the discharge hole to prevent defective discharge of the PLGA solution from the discharge hole, the discharge hole is preferably dipped into the poor solvent. In other words, the discharge hole is preferably in contact with the poor solvent.

Preferably, the discharge hole is dipped into the poor solvent for a depth of from 1.0 to 10 mm, and more preferably from 2.0 to 5.0 mm.

Solution Discharger

The discharge hole may be provided to a solution discharger.

Specific examples of the solution discharger are listed below, but not limited thereto.
  (i) A plate nozzle discharger, such as an inkjet nozzle, that discharges a solution from holes formed on a plate with a pressure.
  (ii) A discharger that discharges a solution from holes formed on a substance having an unstable shape, such as an SPG membrane, with a pressure.
  (iii) A discharger that discharges a solution from holes as liquid droplets while applying a vibration to the solution.

The above discharger (iii) is of several types: film-vibration-type dischargers, Rayleigh-fission-type dischargers, liquid-vibration-type dischargers, and liquid-column-resonance-type dischargers. Each of these dischargers may apply a pressure to the solution when discharges the solution. Two or more of these dischargers may be combined.

Examples of the film-vibration-type dischargers include, but are not limited to, a discharger described in JP-2008-292976-A. This discharger includes a thin film having multiple nozzles and a ring-like vibration generator disposed along the periphery of a deformable area of the thin film. The vibration generator is configured to vibrate the thin film.

Examples of the Rayleigh-fission-type dischargers include, but are not limited to, a discharger described in JP-4647506-B (corresponding to JP-2007-199463-A). This discharger is configured to discharge a liquid from through holes to form liquid droplets. Specifically, the liquid is supplied to a storage, and a vibrator in contact with a part of the storage applies a vibration to the storage, so that the liquid is discharged from multiple through holes disposed to the storage and formed into liquid droplets via a columnar shape and a constricted shape.

Examples of the liquid-vibration-type dischargers include, but are not limited to, a discharger described in JP-2010-102195-A (corresponding to US2010/0104970A1, the disclosure thereof being incorporated herein by reference). This discharger is configured to discharge a liquid from multiple discharge holes to form liquid droplets. Specifically, the liquid is supplied to a storage equipped with a film on which multiple discharge holes are formed and resonated therein, so that the liquid is discharged from the discharge holes and formed into liquid droplets.

Among these dischargers, liquid-column-resonance-type dischargers, employing a liquid column resonance method, combined with a pressure applicator are preferable.

The liquid column resonance method may include the processes of applying a vibration to a PLGA solution contained in a liquid-column-resonant liquid chamber to form a liquid-column-resonant standing wave; and discharging the PLGA solution from discharge holes formed within an area corresponding to an antinode of the liquid-column-resonant standing wave in a direction of vibration of the standing wave. The liquid column resonance method is preferably performed by a liquid-column-resonant liquid droplet discharger Poor Solvent The poor solvent has no limitation. Specific preferred examples of the poor solvent include water. The poor solvent may contain a stabilizer for more improving stability of the resulting particulate PLGA.

Specific examples of the stabilizer include, but are not limited to, hydroxypropyl cellulose (HPC), hydroxypropyl methylcellulose (HPMC), and polyvinyl alcohol (PVA).

Preferably, the concentration of the stabilizer is 5% by mass or less Specific examples of the poor solvent include, but are not limited to, an aqueous solution of PVA.

Liquid Flow Treatment

The liquid flow treatment is performed when the PLGA solution is discharged into the poor solvent. Preferably, the flow rate of the poor solvent becomes 0.3 m/s or more, more preferably 1.0 m/s, by the liquid flow treatment.

The liquid flow treatment suppresses coalescence of PLGA particles.

Means for letting the poor solvent to flow may be a stirrer. Specific examples of the stirrer include, but are not limited to, a stirring blade.

Liquid Circulation Treatment

In the particle forming process, preferably, the poor solvent is circulated while the PLGA solution is discharged from the discharge hole into the poor solvent, for preventing coalescence of PLGA particles.

Therefore, a liquid circulation treatment is preferably performed for circulating the poor solvent.

The liquid circulation treatment may circulate the poor solvent within a poor solvent storage having a circulation channel by using a pump serving as a circulator.

Good Solvent Removing Treatment

In a case in which the poor solvent is circulated, the good solvent of the PLGA is accumulated in the poor solvent. As the good solvent is accumulated in the poor solvent, PLGA particles easily get coalesced with each other. Therefore, a good solvent removing treatment is preferably performed for removing the good solvent from within the circulated poor solvent.

The good solvent removing treatment may remove the good solvent from within the poor solvent by heating the poor solvent or decompressing the poor solvent to vaporize the good solvent.

Other Processes

The method for manufacturing particulate PLGA may further include other processes such as a good solvent removing process and a filtration sterilization process.

Good Solvent Removing Process

The good solvent removing process is a process for removing the good solvent from the resulting particulate PLGA. The good solvent removing process may include subjecting a solution containing the particulate PLGA to a decompression treatment to volatilize only the good solvent and obtain a suspension liquid of the particulate PLGA.

Filtration Sterilization Process

The filtration sterilization process is a process for filtering the suspension liquid with a sterilization filter after the good solvent removing process.

The suspension liquid may be either diluted or undiluted with the poor solvent before being subjected to the filtration.

Preferably, the suspension liquid is applied with ultrasonic waves before being subjected to the filtration. In this case, aggregation of PLGA particles in the suspension liquid is loosen and the PLGA particles are allowed to easily pass through the filter.

Specific examples of the sterilization filter include, but are not limited to, nylon membrane filters.

The filtration accuracy of the sterilization filter is preferably in the range of from 0.1 to 0.45 μm.

The sterilization filter is commercially available Specific examples of commercially-available products of the sterilization filter include, but are not limited to, LifeASSURE™ nylon membrane filter cartridge (filtration accuracy: 0.1 μm, available from 3M).

Particulate PLGA Manufacturing Apparatus

The particulate PLGA manufacturing apparatus in accordance with some embodiments of the present invention includes at least a PLGA solution storage and a solution discharger. The apparatus preferably includes a poor solvent storage and a liquid flow unit, and optionally includes other members.

PLGA Solution Storage

The PLGA solution storage is a container for storing the PLGA solution. The PLGA solution storage may or may not have flexibility.

The PLGA solution storage is not limited in material, and may be made of either a resin or a metal.

The PLGA solution storage is not limited in configuration, and may be made of either an airtight container or a non-airtight container.

In the PLGA solution, the poly(lactic-co-glycolic) acid (PLGA) is dissolved in a good solvent of the PLGA.

Solution Discharger

The solution discharger has at least one discharge hole having an inner diameter of less than 1.0 mm.

The solution discharger is connected to the PLGA solution storage. The connecting method between the solution discharger and the PLGA solution storage has no limitation so long as the PLGA solution can be supplied from the PLGA solution storage to the solution discharger. The solution discharger and the PLGA solution storage may be connected to each other via a pipe or tube.

Preferably, the solution discharger is equipped with a vibration applicator that applies a vibration to the PLGA solution.

Poor Solvent Storage

The poor solvent storage is a member for storing the poor solvent of the PLGA. The poor solvent storage may or may not have flexibility.

The poor solvent storage is not limited in material, and may be made of either a resin or a metal.

The poor solvent stored in the poor solvent storage may or may not be stirred while the particulate PLGA is being manufactured. Preferably, the poor solvent is stirred.

The discharge hole of the solution discharger may or may not be dipped into the poor solvent stored in the poor solvent storage. To prevent the PLGA solution from being dried within the discharge hole to prevent defective discharge of the PLGA solution from the discharge hole, the discharge hole is preferably dipped into the poor solvent. In other words, the discharge hole of the solution discharger is preferably in contact with the poor solvent stored in the poor solvent storage.

Preferably, the discharge hole of the solution discharger is dipped into the poor solvent stored in the poor solvent storage for a depth of from 1.0 to 10 mm, and more preferably from 2.0 to 5.0 mm.

Preferably, the poor solvent storage has a circulation channel capable of circulating the poor solvent. The circulation channel may consist of a piping alone or both a piping and a tank.

Good Solvent Remover

In a case in which the poor solvent is circulated, the good solvent of the PLGA is accumulated in the poor solvent. As the good solvent is accumulated in the poor solvent, PLGA particles easily get coalesced with each other. Therefore, a good solvent remover is preferably provided for removing the good solvent from within the circulated poor solvent.

The good solvent remover removes the good solvent from within the poor solvent. Specific examples of the good solvent remover include a heater for heating the poor solvent and a decompressor for decompressing the poor solvent. By using at least one of the heater and the decompressor, the good solvent can be vaporized and removed from within the poor solvent.

Liquid Flow Unit

The liquid flow unit is configured to let the poor solvent stored in the poor solvent storage to flow. Specific examples of the liquid flow unit include a stirrer for stirring the poor solvent, but are not limited thereto.

The liquid flow unit suppresses coalescence of PLGA particles.

The particulate PLGA in accordance with some embodiments of the present 2.5 invention and a particulate PLGA manufactured the by the method for manufacturing particulate PLGA or the particulate PLGA manufacturing apparatus in accordance with some embodiments of the present invention are suitable for filtration sterilization.

Filtration sterilization is generally performed to remove bacteria, such as microbes, from sterilization objects by using a membrane filter having a pore diameter of 0.1 μm. Therefore, nano PLGA particles having a particle diameter of 200 nm or above cannot sufficiently pass through the filtration sterilization filter.

A liquid-column-resonant liquid droplet discharger, as one example of the solution discharger, is described in detail below.

Figure 1:
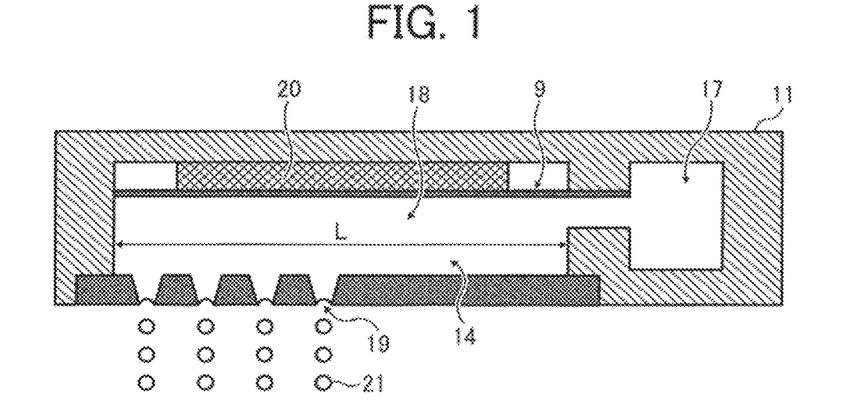
FIG. 1 is a cross-sectional view of a liquid-column-resonant liquid droplet discharger in accordance with some embodiments of the present invention.

FIG. 1 is a cross-sectional view of a liquid-column-resonant liquid droplet discharger 11. The liquid-columnresonant liquid droplet discharger 1 has a liquid common supply channel 17 and a liquid-column-resonant liquid chamber 18. The liquid-column-resonant liquid chamber 18 is communicated with the liquid common supply channel 17 disposed on its one end wall surface in a longitudinal direction. The liquid-column-resonant liquid chamber 18 has discharge holes 19 that discharge liquid droplets 21, on its one wall surface which is connected with its both longitudinal end wall surfaces. The liquid-column-resonant liquid chamber 18 also has a vibration generator 20 that generates high-frequency vibration for forming a liquid-column-resonant standing wave, on the wall surface facing the discharge holes 19. The vibration generator 20 is connected to a high-frequency power source.

A PLGA solution 14 is let to flow into the liquid common supply channel 17 through a liquid supply tube by a liquid circulating pump and is supplied to the liquid-column-resonant liquid chamber 18 disposed within the liquid-column-resonant liquid droplet discharger 11. Within the liquid-column-resonant liquid chamber 18 filled with the PLGA solution 14, the vibration generator 20 generates a liquid-column-resonant standing wave, thereby forming a pressure distribution. The liquid droplets 21 are discharged from the discharge holes 19 provided within an area corresponding to an antinode of the liquid-column-resonant standing wave where the amplitude in pressure variation is large. The area corresponding to an antinode of the liquid-column-resonant standing wave is an area non-corresponding to a node thereof. Preferably, the area corresponding to an antinode is an area where the amplitude in pressure variation of the standing wave is large enough to discharge liquid droplets, more preferably, an area extending from a position at a local maximum amplitude of a pressure standing wave (i.e., a node of a velocity standing wave) toward a position at a local minimum amplitude for a distance±¼ of the wavelength.

Within the area corresponding to an antinode of the pressure standing wave, even in a case in which multiple discharge holes are provided, each of the multiple discharge holes can discharge uniform liquid droplets at a high degree of efficiency without causing clogging. A pan of the PLGA solution 14 that has passed by the liquid common supply channel 17 without being discharged from the discharge holes 19 flows into a liquid return pipe to circulate again.

As the liquid droplets 21 are discharged, the amount of the PLGA solution 14 in the liquid-column-resonant liquid chamber 18 is reduced and a suction force generated by the action of the liquid-column-resonant standing wave is also reduced within the liquid-column-resonant liquid chamber 18. Thus, the flow rate of the PLGA solution 14 supplied from the liquid common supply channel 17 is temporarily increased to fill the liquid-column-resonant liquid chamber 18 with the PLGA solution 14. After the liquid-column-resonant liquid chamber 18 is refilled with the PLGA solution 14, the flow rate of the PLGA solution 14 within the liquid common supply channel 17 is returned.

The liquid-column-resonant liquid chamber 18 may be formed of joined frames made of a material having a high stiffness that does not adversely affect liquid resonant frequency of the liquid at drive frequency, such as metals, ceramics, and silicone. A length L between both longitudinal ends of the liquid-column-resonant liquid chamber 18, illustrated in FIG. 1, is determined based on a mechanism of liquid column resonance. Preferably, a plurality of multiple liquid-column-resonant liquid chambers 18 is provided to a single liquid droplet formation unit to drastically improve productivity Preferably, the number of the liquid-column-resonant liquid chambers 18 is from 1 to 2,000. Each of the liquid-column-resonant liquid chambers 18 is communicated with the liquid common supply channel 17 through each liquid supply channel. The liquid common supply channel 17 is communicated with multiple liquid-column-resonant liquid chambers 18.

The vibration generator 20 is not limited to any particular device so long as it can be driven at a specific frequency. For example, the vibration generator 20 may be formed of a piezoelectric body and an elastic plate 9 attached to each other. The drive frequency of the vibration generator 20 is preferably 150 kHz or more, more preferably from 300 to 500 kHz, for improving productivity. The elastic plate 9 constitutes a part of the wall of the liquid-column-resonant liquid chamber 18 so that the piezoelectric body does not contact the liquid. The piezoelectric body may be made of a piezoelectric ceramic, such as lead zirconate titanate (PZT), which is generally laminated because of having a small displacement. The piezoelectric body may also be made of a piezoelectric polymer such as polyvinylidene fluoride (PVDF), crystal, or a single crystal of $LiNbO_3$, $LiTaO_3$, or $KNbO_3$. Preferably, the vibration generator 20 in each liquid-column-resonant liquid chamber 18 is independently controllable. Alternatively, a single blockish vibrating material may be partially cut to fit the arrangement of the liquid-column-resonant liquid chambers 18 so that each liquid-column-resonant liquid chamber 18 is independently controllable through the elastic plate.

Preferably, the discharge holes 19 are arranged in a width direction of the liquid-column-resonant liquid chamber 18, so that a larger number of discharge holes 19 can be provided for improving production efficiency. Since the liquid-column-resonant frequency varies depending on the arrangement of the discharge holes 19, the liquid column resonant frequency is preferably adjusted monitoring the discharge condition of liquid droplets.

A mechanism of liquid droplet formation based on liquid column resonance is described in, for example, [0011]-[0020] of JP-2011-194675-A (corresponding to US2013/0010035A1, the disclosure thereof being incorporated herein by reference).

One example of the particulate PLGA manufacturing apparatus in accordance with some embodiments of the present invention is described in detail below.

Figure 2:
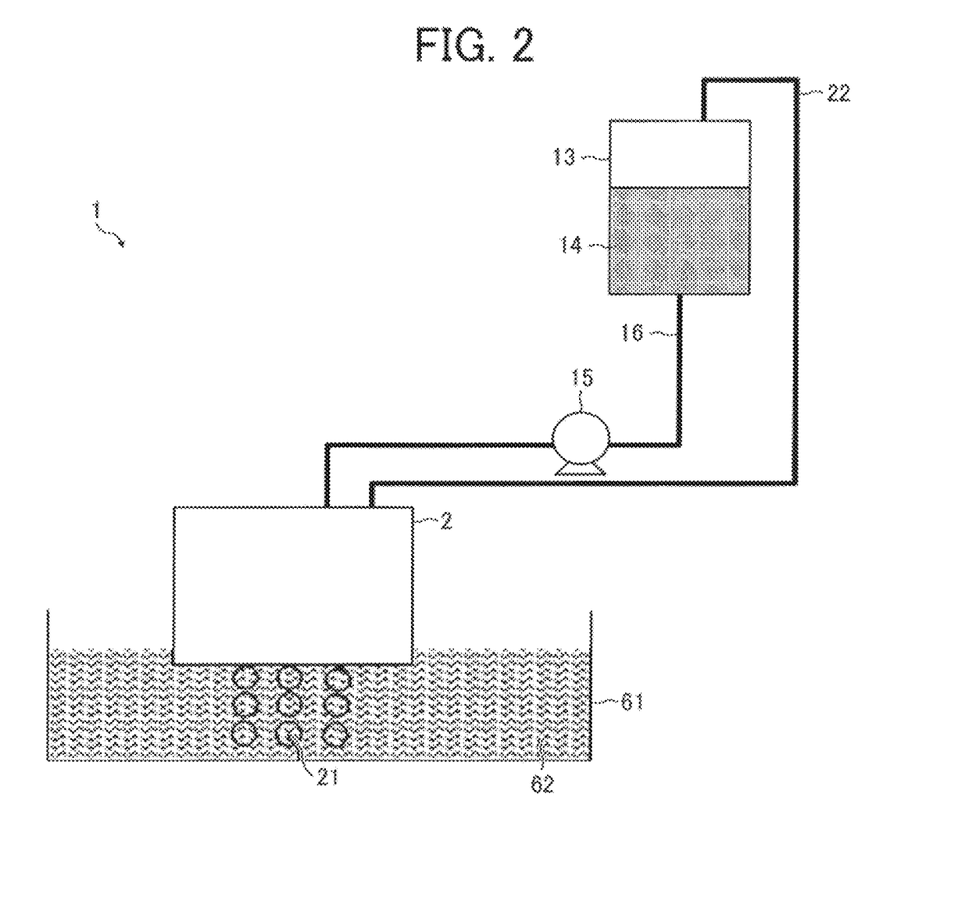
FIG. 2 is a schematic view of a particulate PLGA manufacturing apparatus in accordance with some embodiments of the present invention.

FIG. 2 is a schematic view of a particulate PLGA manufacturing apparatus 1. The particulate PLGA manufacturing apparatus 1 includes a PLGA solution storage 13, a solution discharger 2, and a poor solvent storage 61 as major components. The solution discharger 2 is connected to the PLGA solution storage 13 storing a PLGA solution 14. The solution discharger 2 is further connected to a liquid circulation pump 15 for supplying the PLGA solution 14 stored in the PLGA solution storage 13 to the solution discharger 2 via a liquid supply pipe 16 and for pumping the PLGA solution 14 within the liquid supply pipe 16 to return the PLGA solution 14 to the PLGA solution storage 13 via a liquid return pipe 22. The PLGA solution 14 can be constantly supplied to the solution discharger 2.

The solution discharger 2 may be equipped with the liquid-column-resonant liquid droplet discharger 11 illustrated in FIG. 1.

The PLGA solution 14 is discharged from the solution discharger 2 as liquid droplets 21 into a poor solvent 62 stored in the poor solvent storage 61.

As the liquid droplets 21 and the poor solvent 62 come into contact with each other, the PLGA solution diffuses and the PLGA comes into contact with the poor solvent. As a result, the PLGA crystallizes to become fine spherical particles.

Another example of the particulate PLGA manufacturing apparatus in accordance with some embodiments of the present invention is described in detail below.

Figure 3:
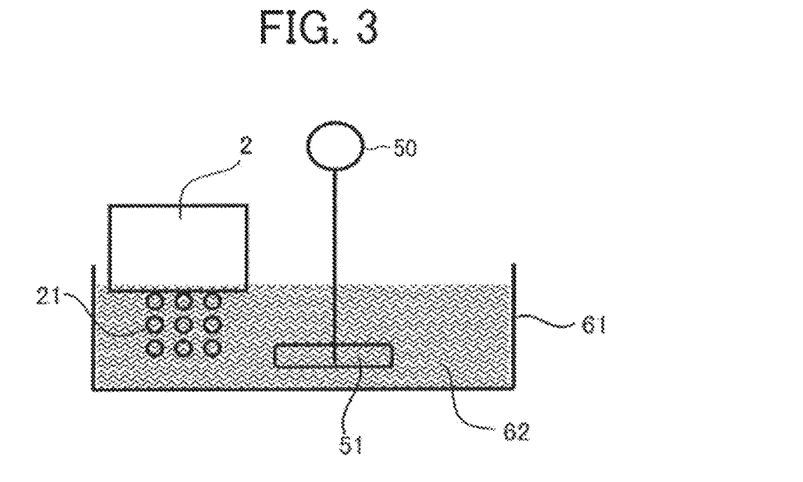
FIG. 3 is a schematic view of a particulate PLGA manufacturing apparatus in accordance with some embodiments of the present invention.

FIG. 3 is a schematic view of a particulate PLGA manufacturing apparatus equipped with a stirrer.

Referring to FIG. 3, the PLGA solution is discharged into the poor solvent 62 stored in the poor solvent storage 61 that is a glass container. The PLGA solution is discharged into the poor solvent 62 with the discharge holes of the solution discharger 2 dipped in the poor solvent 62.

The particulate PLGA manufacturing apparatus illustrated in FIG. 3 is equipped with a stirrer 50 having a stirring blade 51. The stirring blade 51 is dipped in the poor solvent 62 stored in the poor solvent storage 61.

While the PLGA solution is discharged from the solution discharger 2 into the poor solvent 62, the stirring blade 51 is rotated to stir the poor solvent 62, thus preventing coalescence of PLGA particles formed from the liquid droplets 21.

Another example of the particulate PLGA manufacturing apparatus in accordance with some embodiments of the present invention is described in detail below.

One technique for preventing coalescence of PLGA particles, formed upon contact of the PLGA solution with the poor solvent, is to form a flow of the poor solvent at the discharge holes of the solution discharger.

Figure 4A:
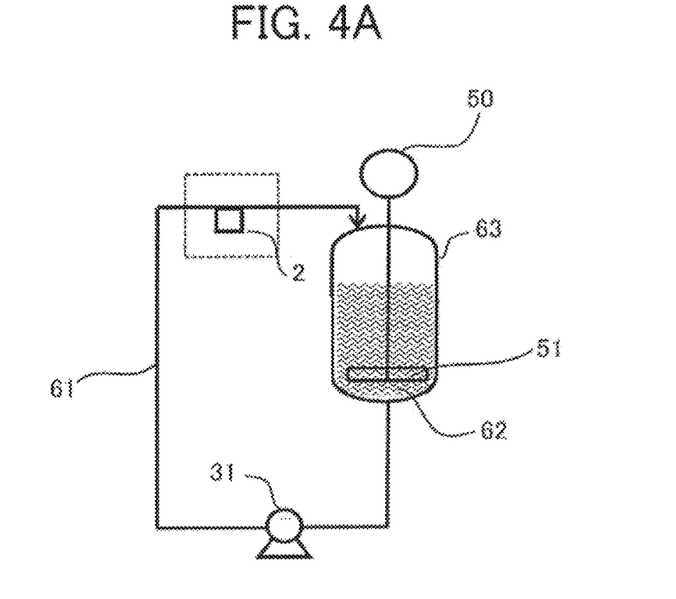
FIG. 4A is a schematic view of a particulate PLGA manufacturing apparatus in accordance with some embodiments of the present invention.

FIG. 4A is a schematic view of a particulate PLGA manufacturing apparatus capable of forming a flow of the poor solvent at the discharge holes of the solution discharger.

The particulate PLGA manufacturing apparatus illustrated in FIG. 4A includes a solution discharger 2, a poor solvent storage 61, a stirrer 50, and a pump 31.

The poor solvent storage 61 includes a circulation channel capable of circulating liquids and a tank 63 disposed on the circulation channel.

Figure 4B:
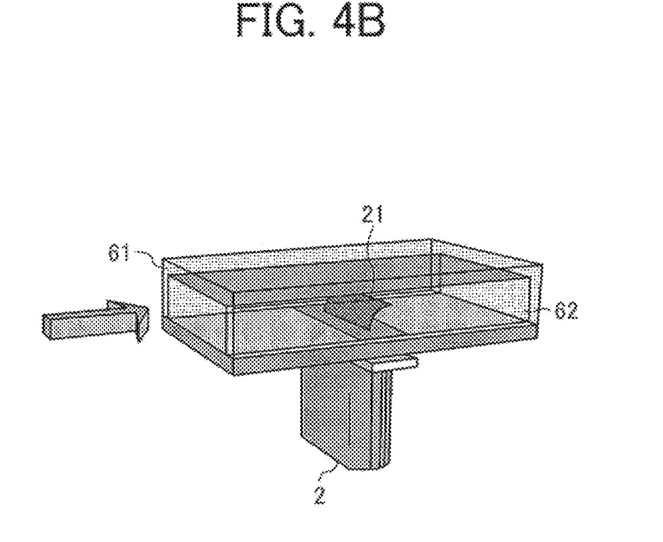
FIG. 4B is a magnified view of a solution discharger and periphery thereof in the particulate PLGA manufacturing apparatus illustrated in FIG. 4A.

FIG. 4B is a magnified view of the solution discharger 2 and periphery thereof (enclosed by dotted lines) illustrated in FIG. 4A.

The poor solvent 62 is poured into the tank 63 and circulated by the pump 31 within the poor solvent storage 61 via the solution discharger 2. During circulation of the poor solvent 62, the PLGA solution is discharged from the discharge holes of the solution discharger 2 into the poor solvent 62. As a flow of the poor solvent 62 is formed, PLGA particles, formed from the liquid droplets 21, are suppressed from coalescing with each other. Preferably, the flow rate of the poor solvent 62 at the discharge holes of the solution discharger 2 is in the range of from 0.3 to 1.0 m/s.

The tank 63 is equipped with the stirrer 50 having a stirring blade 51. As the stirring blade 51 stirs the poor solvent 62, PLGA particles are more suppressed from coalescing with each other.

Another example of the particulate PLGA manufacturing apparatus in accordance with some embodiments of the present invention is described in detail below.

As the content of the good solvent in the poor solvent is increased, PLGA particles more easily get coalesced with each other to become coarse particles. To prevent such a phenomenon, preferably, the good solvent is removed from within the poor solvent and keeping the content of the good solvent in the poor solvent as small as possible.

Figure 5:
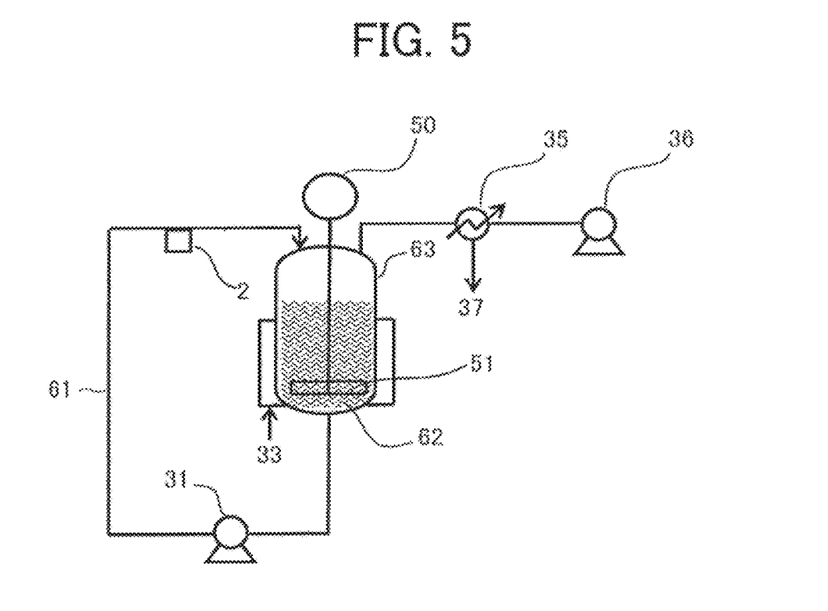
FIG. 5 is a schematic view of a particulate PLGA manufacturing apparatus in accordance with some embodiments of the present invention.

FIG. 5 is a schematic view of a particulate PLGA manufacturing apparatus equipped with a good solvent remover.

The particulate PLGA manufacturing apparatus illustrated in FIG. 5 includes a solution discharger 2, a poor solvent storage 61, a stirrer 50, a pump 31, a heater 33, and a decompressor (vacuum pump) 36. The heater 33 and the decompressor 36 serve as the good solvent remover.

The solution discharger 2 and periphery thereof have the same configuration as those illustrated in FIGS. 4A and 4B.

The poor solvent storage 61 includes a circulation channel capable of circulating liquids and a tank 63 disposed on the circulation channel.

The poor solvent 62 is poured into the tank 63 and circulated by the pump 31 within the poor solvent storage 61 via the solution discharger 2. During circulation of the poor solvent 62, the PLGA solution is discharged from the discharge holes of the solution discharger 2 into the poor solvent 62. As a flow of the poor solvent 62 is formed, PLGA panicles, formed from the liquid droplets 21, are suppressed from coalescing with each other.

The good solvent is removed from within the poor solvent 62 by the actions of the heater 33 and the decompressor 36 provided to the tank 63. For example, the heater 33 may heat the poor solvent 62 and the decompressor 36 may decompress the poor solvent 62 at the same time, so that the good solvent, having a lower boiling point than the poor solvent, is vaporized. The vaporized good solvent is condensed by a condenser 35 and collected via a collection pipe 37.

EXAMPLES

Further understanding can be obtained by reference to certain specific examples which are provided herein for the purpose of illustration only and are not intended to be limiting.

Example 1

Preparation of PLGA Solution

A poly(lactic-co-glycolic) acid (PLGA 7510 available from Wako Pure Chemical Industries, Ltd.) was dissolved in a mixture solvent of acetone and ethanol (mixed at a mass ratio of 1:1) with a stirrer to obtain a PLGA solution having a concentration of 0.3% by mass.

Next, 0.15 g of a polyvinyl alcohol (PVA 363170 available from Sigma-Aldrich) was dissolved in 49.85 g of ion-exchange water to prepare a PVA aqueous solution having a concentration of 0.3% by mass, serving as a poor solvent of the PLGA. The PVA aqueous solution was poured into the poor solvent storage 61 made of glass illustrated in FIG. 3.

Preparation of Particulate PLGA

The PLGA solution in an amount of 1 g was discharged into the poor solvent (i.e., the PVA aqueous solution having a concentration of 0.3% by mass) using the particulate PLGA manufacturing apparatus illustrated in FIG. 3 equipped with the liquid-column-resonant discharger illustrated in FIG. 1, while the stirrer 50 was rotated at a revolution of 200 rpm. Thus, a liquid containing PLGA nano particles was prepared. At this time, the temperature of the poor solvent was 25° C.

Nozzle (i.e., discharge hole) inner diameter: 8.0 μm
Liquid feed pressure: 0.03 MPa
Solution discharger: Liquid-column-resonant type
Drive frequency: 150 kHz
Applied voltage to piezoelectric body: 5.0 V
Immersion depth of nozzles (i.e., discharge holes) in poor solvent: 3.0 mm Removal of Good Solvent While the liquid was stirred at a revolution of 200 rpm, a decompression treatment was performed at −50 kPa for 24 hours to remove the good solvent (i.e., mixture of acetone and ethanol) therefrom. Thus, a particulate PLGA suspension liquid was prepared.

Evaluation of Particle Size Distribution

Figure 6:
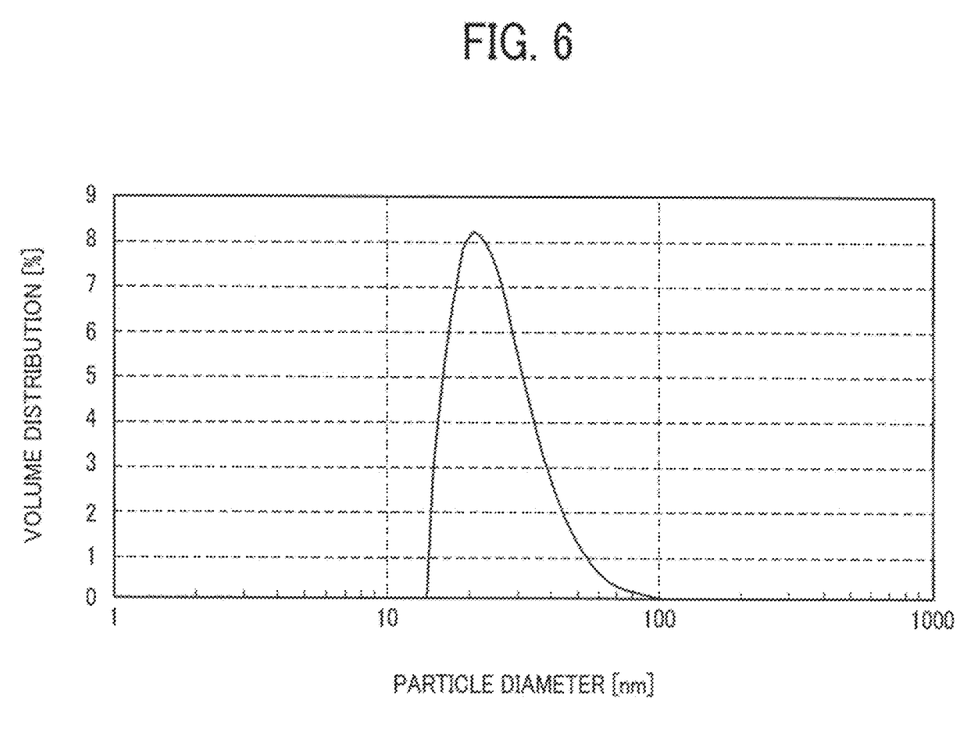
FIG. 6 is a graph showing a particle size distribution of particles prepared in Example 1.

The particulate PLGA suspension liquid was subjected to a measurement by a Fiber-Optics Particle Analyzer (FPAR-1000) available form Otsuka Electronics Co., Ltd.) employing a dynamic light scattering method for measuring thick systems, to determine average volume-based particle diameter and R.S.F. The results are presented in Table 1. The particle size distribution is illustrated in FIG. 6.

The concentration of the particulate PLGA in the particulate PLGA suspension liquid was adjusted to 0.1% by mass before the measurement. The integrating time per measurement was 180 seconds. The average volume-based particle diameter (nm) was determined by a Contin method. The measurement was repeated three times and the measured average volume-based particle diameter values (nm) were averaged.

The average volume-based particle diameter and R.S.F. thus determined were evaluated based on the following criteria.

Evaluation Criteria
For Average Volume-based Particle Diameter
A: The average volume-based particle diameter was from 10 nm to 50 nm.
B: The average volume-based particle diameter was greater than 50 nm but not greater than 80 nm.
C: The average volume-based particle diameter was greater than 80 nm.

For R.S F.
A. R.S.F was greater than 0 but not greater than 1.00.
B: R.S.F. was greater than 1.00 but not greater than 1.20.
C: R.S.F. was greater than 1.20.

Evaluation of Sterilization Rate

The particulate PLGA suspension liquid was filtered with a nylon membrane filter for sterilization having a pore diameter of 0.1 μm (PSA available from 3M). After the filtration sterilization, the filtrate was sufficiently dried in a drying oven at 50° C. and the weight of the residual PLGA was measured to calculate sterilization rate. The results were presented in Table 1.

The sterilization rate was calculated by the following formula and evaluated based on the following criteria.

Sterilization Rate (%)=((Weight of Dried PLGA after Filtration)/(Weight of PLGA in Suspension Liquid before Filtration))×100

Evaluation Criteria
A: The sterilization rate was 90% or more.
B: The sterilization rate was not less than 70% but less than 90%.
C: The sterilization rate was less than 70%.

Example 2

The procedure in Example 1 for preparing a particulate PLGA was repeated except for changing the PLGA concentration in the PLGA solution from 0.3% to 1.0% by mass and the nozzle diameter from 8.0 μm to 50 μm.

The measurement of average volume-based particle diameter and R.S.F. and the evaluation of sterilization rate were performed in the same manner as in Example 1 The results were presented in Table 1.

Example 3

The procedure in Example 1 for preparing a particulate PLGA was repeated except for changing the nozzle diameter from 8.0 μm to 100 μm.

The measurement of average volume-based particle diameter and R.S.F. and the evaluation of sterilization rate were performed in the same manner as in Example 1 The results were presented in Table 1.

Example 4

The procedure in Example 1 for preparing a particulate PLGA was repeated except for changing the nozzle diameter from 8.0 μm to 500 μm.

The measurement of average volume-based particle diameter and R.S.F. and the evaluation of sterilization rate were performed in the same manner as in Example 1 The results were presented in Table 1.

Example 5

The procedure in Example 1 for preparing a particulate PLGA was repeated except for adding cyclosporine (CYCLOSPORINE available from Tokyo Chemical Industry Co, Ltd.) to the PLGA solution in an amount of 5% based on the mass of the PLGA.

The measurement of average volume-based particle diameter and R.S.F. and the evaluation of sterilization rate were performed in the same manner as in Example 1 The results were presented in Table 1.

Example 6

The procedure in Example 1 for preparing a particulate PLGA was repeated except for replacing the liquid-column-resonant-type solution discharger with another solution discharger that discharges a solution from a plate nozzle without applying vibration.

The measurement of average volume-based particle diameter and R.S.F. and the evaluation of sterilization rate were performed in the same manner as in Example 1. The results were presented in Table 1.

Example 7

The procedure in Example 6 for preparing a particulate PLGA was repeated except for changing the nozzle diameter from 8.0 μm to 50 μm and the PLGA concentration in the PLGA solution from 0.3% to 1.0% by mass, and adding cyclosporine (CYCLOSPORINE available from Tokyo Chemical Industry Co., Ltd.) to the PLGA solution in an amount of 5% based on the mass of the PLGA.

The measurement of average volume-based particle diameter and R.S F, and the evaluation of sterilization rate were performed in the same manner as in Example 6. The results were presented in Table 1.

Example 8

The procedure in Example 6 for preparing a particulate PLGA was repeated except for changing the manufacturing apparatus with another manufacturing apparatus illustrated in FIGS. 4A and 4B.

The tank 63 was a 300-mL tank capable of heating hot water. Hot water having a temperature of 25'C was let to flow therein. The stirrer 50 was a paddle-type stirrer. The stirring blade 51 was rotated at a revolution of 200 rpm. The pump 31 was a UOD (product name) available from Nikuni Co., Ltd. The flow rate of the poor solvent at the discharge holes of the solution discharger 2 was 1.0 m/s.

The measurement of average volume-based particle diameter and R.S.F. and the evaluation of sterilization rate were performed in the same manner as in Example 6. The results were presented in Table 1.

Example 9

The procedure in Example 6 for preparing a particulate PLGA was repeated except for changing the manufacturing apparatus with another manufacturing apparatus illustrated in FIG. 5.

The tank 63 was a 300-mL tank capable of heating hot water. Hot water having a temperature of 40° C. was let to flow therein. The stirrer 50 was a paddle-type stirrer. The stirring blade 51 was rotated at a revolution of 200 rpm. The pump 31 was a UOD (product name) available from Nikuni Co., Ltd. The flow rate of the poor solvent at the discharge holes of the solution discharger 2 was 1.0 m/s. The condenser 35 was a Mini Spiral Heat Exchanger KMSB available from Kurose Chemical Equipment Co., Ltd. The decompressor 36 was a vacuum pump CV-2E available from Osaka Air Machine, Inc. During operation, the temperature of the poor solvent was 25° C. A particulate PLGA was obtained by removing the good solvent from within the poor solvent.

The measurement of average volume-based particle diameter and R.S.F. and the evaluation of sterilization rate were performed in the same manner as in Example 6 The results were presented in Table 1.

Comparative Example 1

The procedure in Example 1 for preparing a particulate PLGA was repeated except for replacing the liquid-column-resonant-type solution discharger with a Teflon® tube having an inner diameter of 1.0 mm.

The measurement of average volume-based particle diameter and R.S.F. and the evaluation of sterilization rate were performed in the same manner as in Example 1 The results were presented in Table 1.

Comparative Example 2

The procedure in Comparative Example 1 for preparing a particulate PLGA was repeated except for changing the PLGA concentration in the PLGA solution from 0.3% to 0.0% by mass.

The measurement of average volume-based particle diameter and R.S.F. and the evaluation of sterilization rate were performed in the same manner as in Comparative Example 1. The results were presented in Table 1.

Comparative Example 3

The procedure in Comparative Example 2 for preparing a particulate PLGA was repeated except for changing the inner diameter of the Teflon™ tube from 1.0 mm to 2.5 mm.

The measurement of average volume-based particle diameter and R.S.F. and the evaluation of sterilization rate were performed in the same manner as in Comparative Example 2. The results were presented in Table.

Comparative Example 4

The procedure in Example 1 for preparing a particulate PLGA was repeated except for replacing the liquid-column-resonant-type solution discharger with a Teflon™ tube having an inner diameter of 5.0 mm and changing the PLGA concentration in the PLGA solution from 0.3% to 0.1% by mass.

The measurement of average volume-based particle diameter and R.S.F. and the evaluation of sterilization rate were performed in the same manner as in Example 1. The results were presented in Table 1.

TABLE 1

| | | Discharger | Nozzle Inner Diameter | Flow of Poor Solvent | Removal of Good Solvent | Physiologically Active Substance | PLGA Conc. (% by mass) | Average Volume-based Particle Diameter (nm) | | R.S.F | | Sterilization Rate (%) | |
|---|---|---|---|---|---|---|---|---|---|---|---|---|---|
| | | | | | | | | | Rank | | Rank | | Rank |
| Examples | 1 | Liquid Column Resonance | 8.0 μm | No | No | N/A | 0.3 | 16.7 | A | 1.15 | B | 99.9 | A |
| | 2 | Liquid Column Resonance | 50 μm | No | No | N/A | 1.0 | 65.4 | B | 1.09 | B | 98.2 | A |
| | 3 | Liquid Column Resonance | 100 μm | No | No | N/A | 0.3 | 74.2 | B | 1.08 | B | 81.2 | B |
| | 4 | Liquid Column Resonance | 500 μm | No | No | N/A | 0.3 | 79.8 | B | 1.01 | B | 78.1 | B |
| | 5 | Liquid Column Resonance | 8.0 μm | No | No | Cyclosporine | 0.3 | 19.0 | A | 1.18 | B | 99.8 | A |
| | 6 | Plate Nozzle | 8.0 μm | No | No | N/A | 0.3 | 27.8 | A | 1.18 | B | 99.1 | A |
| | 7 | Plate Nozzle | 50 μm | No | No | Cyclosporine | 1.0 | 68.7 | B | 1.18 | B | 88.1 | B |
| | 8 | Plate Nozzle | 8.0 μm | 1.0 m/s | No | N/A | 0.3 | 25.1 | A | 1.15 | B | 98.2 | A |
| | 9 | Plate Nozzle | 8.0 μm | 1.0 m/s | Yes | N/A | 0.3 | 24.2 | A | 0.98 | A | 99.1 | A |

TABLE 1-continued

| | | Discharger | Nozzle Inner Diameter | Flow of Poor Solvent | Removal of Good Solvent | Physiologically Active Substance | PLGA Conc. (% by mass) | Average Volume-based Particle Diameter (nm) | | R.S.F | | Sterilization Rate (%) | |
|---|---|---|---|---|---|---|---|---|---|---|---|---|---|
| | | | | | | | | (nm) | Rank | | Rank | (%) | Rank |
| Comparative Examples | 1 | Tube | 1.0 mm | No | No | N/A | 0.3 | 118 | C | 0.73 | A | 25.2 | C |
| | 2 | Tube | 1.0 mm | No | No | N/A | 0.5 | 129 | C | 0.83 | A | 19.0 | C |
| | 3 | Tube | 2.5 mm | No | No | N/A | 0.5 | 135 | C | 0.79 | A | 18.2 | C |
| | 4 | Tube | 5.0 mm | No | No | N/A | 0.1 | 68.3 | B | 1.24 | C | 57.2 | C |

Numerous additional modifications and variations are possible in light of the above teachings. It is therefore to be understood that, within the scope of the above teachings, the present disclosure may be practiced otherwise than as specifically described herein. With some embodiments having thus been described, it will be obvious that the same may be varied in many ways. Such variations are not to be regarded as a departure from the scope of the present disclosure, and all such modifications are intended to be included within the scope of the present disclosure.

The invention claimed is:

1. A method for manufacturing particulate poly(lactic-co-glycolic) acid (PLGA), comprising:
dissolving a poly(lactic-co-glycolic) acid (PLGA) in a solvent consisting of a good solvent of the PLGA to obtain a PLGA solution;
discharging the PLGA solution from at least one discharge hole having an inner diameter of less than 1.0 mm into a poor solvent of the PLGA; and
forming particulate PLGA having an average volume-based particle diameter of 80 nm or less and a relative span factor (R.S.F.) satisfying the following Formula (I):

$$0 < R.S.F. \leq 1.2 \quad \text{Formula (I)},$$

wherein said good solvent has a PLGA solubility of 0.1 g or more per 100 g of solvent at 25° C., and said poor solvent has a PLGA solubility of at most 0.05 g per 100 g of solvent at 25° C.,
said method is an emulsion solvent diffusion method and, discharging of said solution is performed in a liquid discharger equipped with the at least one discharge hole, a liquid chamber and a vibration generator which applied a vibration to said liquid chamber to cause said PLGA solution to be discharged from said at least one discharge hole.

2. The method of claim 1, wherein the discharging includes letting the poor solvent to flow.

3. The method of claim 2, wherein the poor solvent has a flow rate of 0.3 m/s or more.

4. The method of claim 1, wherein the discharging includes circulating the poor solvent.

5. The method of claim 4, further comprising removing the good solvent from within the circulated poor solvent.

6. The method of claim 1, wherein said particulate PLGA has an average volume-based particle diameter of 10 to 50 nm.

7. The method of claim 1, wherein said particulate PLGA has an average volume-based particle diameter of 10 to 30 nm.

8. The method of claim 1, wherein said PLGA has a weight average molecular weight of from 2,000 to 250,000.

9. The method of claim 1, wherein a molar ratio of structural unites derived from lactic acid to structural units derives from glycolic acid is 50:50 to 85:15.

10. The method of claim 1, wherein a content of PLGA in said PLGA solution is from 0.1 to 5.0% by mass.

11. The method of claim 1, wherein said PLGA solution is discharged into said poor solvent from said discharge hole at a depth of from 1.0 to 10 mm.

12. The method of claim 1, wherein a plurality of discharge holes are disposed on one liquid chamber.

* * * * *